United States Patent [19]

Fishman

[11] Patent Number: 5,046,498

[45] Date of Patent: Sep. 10, 1991

[54] MAGNETIC RESONANCE HUMAN MEDICAL AND VETERINARY IMAGING METHOD

[75] Inventor: Royce S. Fishman, Iselin, N.J.

[73] Assignee: Union Carbide Industrial Gases Technology Corporation, Danbury, Conn.

[21] Appl. No.: 641,789

[22] Filed: Jan. 16, 1991

[51] Int. Cl.$^5$ ............................................. A61B 5/055
[52] U.S. Cl. .................................. 128/653 CA; 424/9
[58] Field of Search .................... 128/653 CA; 424/9; 436/173

[56] References Cited

U.S. PATENT DOCUMENTS 4,586,511  5/1986  Clark, Jr. ...................... 128/653 CA
4,893,627  1/1990  Kehayias et al. ............. 128/653 CA

OTHER PUBLICATIONS

Basic MR Physics, Hendrick et al, Introduction to Magnetic Resonance Imaging, Multi-Media Publishing, Inc., pp. 7-30 (1984).

Primary Examiner—Ruth S. Smith
Attorney, Agent, or Firm—Stanley Ktorides

[57] ABSTRACT

A medical magnetic resonance imaging method for use with human and veterinary patients or subjects employing stable neon to provide contrast enhancement sufficient to provide both qualitative images and quantitative physiological information to assist in diagnosis, physiological challenges, the selection of pharmaceutical or surgical therapy and the assessment of the effectiveness of therapy.

13 Claims, 2 Drawing Sheets

MAGNETIC RESONANCE HUMAN MEDICAL AND VETERINARY IMAGING METHOD

TECHNICAL FIELD

This invention relates generally to magnetic resonance imaging and more specifically to in-vivo contrast enhancement agents for use in magnetic resonance imaging of human or veterinary subjects.

BACKGROUND ART

Medical imaging using X-rays to produce a two dimensional image of internal body structures and detection of disease based on their differential attenuation of X-rays has a long and well documented history. A recent advance in X-ray imaging is computerized tomography (CT) which enables one to produce a tomographic three-dimensional X-ray image with high spatial resolution showing internal structures which might not be easily detected with conventional two dimensional X-ray techniques.

Ionic and non-ionic iodine based contrast enhancement agents are often used with CT to better differentiate between different tissues and compartments and to detect abnormalities. Because iodine has a high atomic number, it absorbs or attenuates X-rays in proportion to its presence. Iodine based contrast enhancement agents are injected intravenously and so their use involves an invasive procedure. The primary use of iodine based contrast enhancement agents is in the diagnosis of disease and appraisal of theraPy concerning the arteriovenous (vascular) system, which they improve the visualization of. Iodine based contrast enhancement agents stay in the vascular system unless the wall of the blood vessel(s) is damaged by disease. They do not normally cross the blood-brain barrier. They are also used to detect abnormalities within the blood vessels such as occlusions (blockages).

While CT uses a highly collimated (focused) beam of X-rays, which minimizes radiation dosage to tissues other than those being examined, radiation dosages are still considered to be high and thus it is desirable to have an imaging method which does not use X-rays. This is especially true with pediatric patients.

Recently magnetic resonance imaging (MRI) was commercially introduced to the medical field. MRI is a three dimensional imaging process. It is based on the same underlying principles as nuclear magnetic resonance (NMR), which has been used for some time in analytical chemistry.

MRI is advantageous over two dimensional and three dimensional CT X-ray techniques in that MRI better defines soft tissue structures. It is also advantageous over X-ray techniques, because it does not require the patient being exposed to X-rays. While energy deposition occurs in the patient because magnetism is electromagnetic energy, it occurs in amounts that using currently authorized MRI magnetic field strengths and imaging methodologies are considered very safe.

As with CT, the likelihood of an accurate diagnosis and assessment of therapeutic impact may be improved in MRI by the use of a contrast enhancement agent. The usefulness of an MRI contrast enhancement agent depends on the physical, chemical and biological properties of the agent and how it distributes within the body in normal and abnormal (diseased) states. However, unlike the iodine based contrast enhancement agents used in CT which produce contrast based on the attenuation of X-rays, a contrast enhancement agent useful with MRI will generate a contrast factor, based on how its atomic structure responds to magnetic fields and one or more MRI imaging methodologies.

At present, only gadopentetate dimeglumine, which must be injected and so is invasive, is authorized for use as a contrast enhancement agent with MRI. Gadopentetate dimeglumine is a highly effective relaxation agent and its use has been authorized to provide contrast enhancement when used with MRI in those intracranial lesions with abnormal vascularity or those thought to cause an abnormality in the blood-brain barrier and to facilitate visualization of intracranial lesions including but not limited to tumors. This contrast enhancer is an intravascular agent and cannot cross the blood-brain barrier unless the blood-brain barrier is damaged. It is also authorized for use in the detection of lesions of the spine. However, potential side effects and adverse reactions exist.

Accordingly, it is an object of this invention to provide an improved magnetic resonance imaging method.

It is another object of this invention to provide an improved magnetic resonance imaging method employing a contrast enhancer which overcomes problems associated with heretofore known methods.

It is a further object of this invention to provide an improved magnetic resonance imaging method employing a contrast enhancement agent which provides improved diagnostic and therapy assessment capabilities.

It is a still further object of this invention to provide a contrast enhancement mixture which may be provided to a living organic subject for improving magnetic resonance imaging.

SUMMARY OF THE INVENTION

The above and other objects which will become apparent to one skilled in the art upon a reading of this disclosure are attained by the present invention one aspect of which is:

A method for carrying out magnetic resonance imaging with improved contrast comprising:

(A) providing a living organic subject having nuclei;

(B) providing stable neon to said subject;

(C) applying a magnetic field to the subject to align at least some of the subject's nuclei;

(D) providing radio energy for absorption and reemission by said aligned nuclei; and (E) gathering data based on the re-emitted radio energy to produce output of medical value in patient management.

Another aspect of the invention comprises:

A mixture, particularly useful for provision to a living organic subject for contrast enhancement in magnetic resonance imaging, said mixture comprising:

(A) from 10 to 80.5 mole percent stable neon;

(B) from 19.5 to 90 mole percent oxygen;

(C) from 0 to 30 mole percent helium;

(D) from 0 to 7 mole percent carbon dioxide; and (E) from 0 to 70.5 mole percent nitrogen.

As used herein the term "stable neon" means the non-radioactive form of neon having an atomic weight of about 20 and an atomic number of 10.

As used herein the term "blood-brain barrier" refers to the fact that the cells of brain capillaries are different from other capillaries, because they form a continuous wall that prevents many substances from entering the brain. The blood-brain barrier is that continuous wall which exists without interruption except in case of disease. Essential nutrients and gases can still cross the normal blood-brain barrier. Molecules that are lipid soluble are easily transported across the blood-brain barrier. Certain gases can diffuse across the blood-brain barrier.

As used herein, the term "in-vivo" refers to being inside the body, as for example a contrast enhancement agent.

As used herein, the term "nucleus" (plural nuclei) means the positively charged central portion of an atom that comprises nearly all of the atomic mass and that consists of protons and neutrons, except in hydrogen, whose nucleus consists of only one proton. The properties of nuclei that are relevant to MRI include their magnetic dipole moments and presence in living tissue. Nuclei possess magnetic dipole moments, meaning they produce a magnetic field themselves and can be affected by an externally imposed magnetic field. The magnetic dipole moments of protons and neutrons pair up and cancel each other out. If a nucleus has an equal number of protons and neutrons, then there is no magnetic dipole moment. If a nucleus has an odd number of protons or neutrons, then a net magnetic dipole moment exists that can be effected by an external magnetic field such as that imposed by MRI. Hydrogen, Carbon 13, Sodium 23 and Phosphorous 31 are examples of nuclei that are both present in living tissue and may be utilized for MRI procedures.

As used herein, "$T_1$ relaxation" (spin-lattice) means the rate of recovery of the longitudinal magnetization described by the longitudinal relaxation time. It is the time required for about 63% of the longitudinal magnetization to recover along the direction of the static magnetic field after a 90° pulse. Different $T_1$ recovery rates exist because different tissues have different concentrations and sizes of macromolecules. $T_1$ weighted images are best for obtaining high resolution anatomy.

As used herein, "$T_2$ relaxation" (spin-spin) means the loss of signal due to inherent tissue effects. It is the time required for the transverse magnetization to decrease to 37% of its original value which it possessed immediately following the 90° pulse. Tissues have different $T_2$ values, mostly due to their differing macromolecular environments. $T_2$ is better than $T_1$ for differentiating tissue and so is effective in detecting disease.

As used herein, "fast or ultrafast scanning" means rapidly obtaining images using gradient echo or field echo pulse seguences. The process eliminates the need to wait for $T_1$ recovery of the longitudinal magnetization after signal measurement. Pulse sequences using less than 90° angles can be repeated as soon as measurement of signal. Total imaging times are in seconds. There are several techniques that have been used in MRI and they are commonly referred to as the FAST technique (Fourier acquired steady state technique), GRASS (gradient recalled acquisition in the steady state), FLASH (fast low angle shot) and FISP (fast imaging with steady state precession).

As used herein, "pulse sequence" refers to how radio-frequency pulses are sent into a patient, how the signals are re-emitted from the patient and how much time exists between the sending and receiving of the pulses. There are many factors that are manipulated by the clinician using the MRI device itself, which allow the pulse sequence to be varied.

As used herein, the term "injection" means the act of forcing a fluid or solution into an artery, vein, cavity or tissue to introduce a gas or solution. Injections are done rapidly over a period of time ranging from seconds to generally less than one minute.

As used herein, the term "infusion" means the introducing of a gas or solution into an artery, vein, cavity or tissue over a long period of time generally measured in minutes.

As used herein, the term "non-invasive" means not requiring breaking the integrity of the body surface such as is required with an injection, to administer a substance. Inhalation of a gas is considered to be a non-invasive procedure, because the gas is inhaled during the normal act of breathing. Procedures that are invasive carry with them added risk of problems at the injection site and the breaking of the sterility of the arterio-venous system.

As used herein, the term "solubility" of a gas means the ability of a substance such as a specific volume of gas to be dissolved in a specific volume of liquid, thereby forming a solution which is a mixture of the two substances.

As used herein, the term "equilibrated solution" means a solution in which the ratio of concentration of gas in a solution equals that of the gas above the solution.

As used herein, the term "saturated solution" means a solution that contains as much of the gas as it can in the presence of an excess of the gas. The saturated solution is then kept in a gas tight sealed container with no gas space and is injected or infused directly into the patient.

As used herein, the term "supersaturated solution" means a solution that goes beyond saturation, because, for example, the pressure and/or temperature is increased so that the amount of gas present in the solution is above that which it would be at standard temperature and pressure. The supersaturated solution is then kept in a gas tight sealed container with no gas space under increased pressure and/or temperature and is injected or infused directly into the patient.

As used herein, a "sealed cartridge" as a form of product packaging means a container impermeable to gas that is filled with stable neon gas or gas mixture or stable neon gas or gas mixture in an equilibrated, saturated or supersaturated liquid solution and then sealed during the production process. The cartridge is used with a device that breaks the seal of the cartridge and allows the injection or infusion of its contents directly into a patient.

As used herein, a "pre-filled syringe" means a form of product packaging where the syringe is made of a material that is impermeable to gas. It is filled with stable neon gas or gas mixture or stable neon gas or gas mixture in an equilibrated, saturated or supersaturated liquid solution and then sealed during the production process. The syringe contains two septa, one in the rear and one in the front, that act after production filling of the syringe as seals to prevent the escape of gas from the inside of the syringe, or the escape of gas from solution by eliminating any space around the liquid. At the time of injection, the front septa is penetrated by an internal extension of the external needle. The pressure from the rear septa moving forward drives the gas or solution out the front needle directly into a patient.

DETAILED DESCRIPTION

Magnetic resonance imaging or MRI takes advantage of the fact that diseased tissue and different types of healthy tissue have a differing molecular arrangement and thus produce a differing image when re-emitting radio wave energy.

Certain types of nuclei, including but not limited to hydrogen nuclei, when placed in a uniform magnetic field, emit a pulse of radiofrequency after they are exposed to a pulse of radiofrequency. . This is referred to as "resonance", can be measured and can provide information about the nuclei that emitted them.

Figure 1:
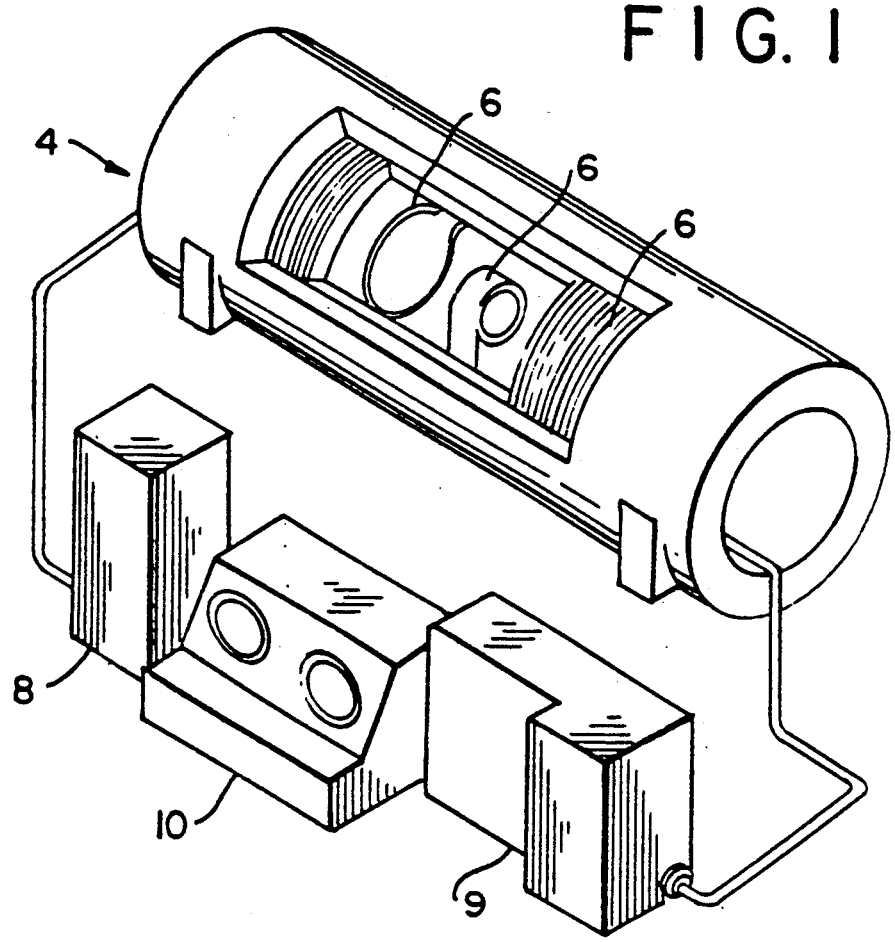
FIG. 1 is a simplified and generic schematic diagram of a superconductive MRI apparatus which may be employed in the practice of this invention. Specific MRI designs vary between manufacturers, from model to model from a single manufacturer, and may use superconductive, permanent or resistive types of magnets.
Figure 2:
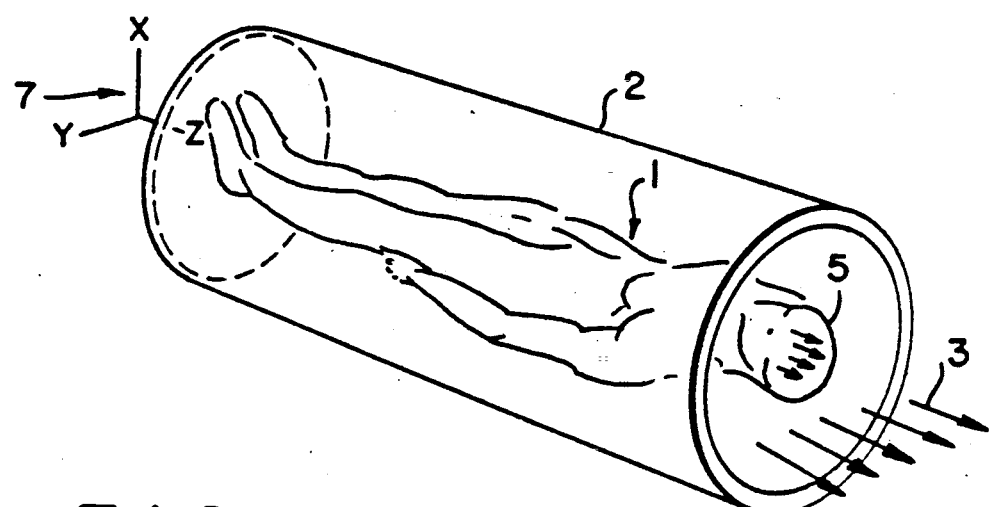
FIG. 2 is a simplified representation of a human subject undergoing MRI treatment with alignment of nuclei.

Referring now to FIGS. 1 and 2, in the practice of MRI, a human or veterinary patient 1 is placed in the center or bore 2 of a magnetic field 3 generated by an MRI system 4. The nuclei in the patient, which are normally randomly arranged, are subjected to a strong magnetic field, which causes some of them to align 5 their spin axes along the magnetic field. Radiofrequency is emitted by coils 6 that are either inside the MRI system near but not on the patient, or that are actually placed on the patient (called surface coils) for imaging smaller more focused areas. The same or additional coils may be used to receive the resonating signal that is emitted by the nuclei. A series of radiofrequency pulses are then emitted by the power supply 8 of the MRI system via these coils. The nuclei in the body absorb this energy and the vector of their magnetization is briefly rotated. When the radiofrequency pulse is turned off, the nuclei return to their previous condition (equilibrium) and in the process of doing so reemit the energy, producing a radiofrequency pulse (resonance) which is collected as data and converted by MRI computer software to useful information having medical value in patient management.

The specific characteristics of the radiofrequency emitted indicate the quantity and nature or state of the atoms in the specific areas of tissue being examined. The source of a specific resonating signal is established as to its location in three dimensions. Additional magnet coils are used to make the field generated by the main magnet vary in small increments along three coordinates 7, which are called gradients. The frequency of the radiofrequency pulse is linked to these magnetic gradients. They allow image reconstruction by the MRI computer software. The information produced is processed by a computer 9 and special software programs to produce, on display 10, of tissues in the body and other information and may be used to derive quantitative information of a physiological nature.

MRI imaging is based on four important parameters. These are proton density, T1, T2 and flow parameters. Pulse sequences made up of radiofrequency pulses can vary in number, the time it takes for the resonance signal to be emitted and the time interval between pulses. The most common pulse sequences are commonly called spin echo, saturation recovery and inversion recovery. Preferably, hydrogen nuclei are imaged because they produce the most powerful response signal and exist in all body tissues, primarily as part of the water molecule.

Water may be bound to protein. The protons of these hydrogen nuclei, which are part of the water molecule, cannot relax as rapidly after absorbing a radiofrequency pulse. This impacts what are termed T1 and T2 relaxation times. T1 indicates the time it takes for equilibrium to be attained again (relaxation) and the loss of energy by the nuclei in question to nearby matter. T2 relates to magnetic spins being different than those around them. This method can be used to detect disease states. Like T1, it is affected by the amount of water present. Relaxation times are usually measured in nanoseconds or milliseconds.

It has been found that after flowing blood is subjected to radiofrequency, that volume or compartment of blood moves in a blood vessel before responding or resonating back radiofrequency. The original site of a specific compartment of blood therefore does not emit a radiofrequency. This factor has been used experimentally to try to quantify regional blood flow via transit time measurements. An effective blood pool contrast enhancement agent would improve the viability of this MRI technique.

There are also MRI methodologies using extremely fast and ultrafast sequences such as but not limited to small angle gradient echo sequences. In addition, variants of echo planar techniques can provide better temporal resolution.

In the practice of this invention, initial baseline MRI images of the patient may optionally be taken without stable neon being provided to the patient, followed by stable neon being provided to the patient so that it is present in-vivo prior to and/or during that part of the MRI procedure whose purpose it is to generate images and information based on the in-vivo presence and distribution of stable neon. The stable neon is provided in an amount sufficient to effectively achieve enhanced contrast results. It has been found that the use of stable neon using, for example, but not necessarily limited to, $T_2$ weighted images, produces what may be termed a "reverse contrast". The reverse contrast produced where stable neon is present is in a high enough ratio to the normal image produced where stable neon is not present, to allow a clear visualization of where it is present and not present. This contrast may be used to better distinguish different normal tissues and compartments from each other, as well as normal from abnormal tissues, compartments and physiology. MRI procedures may be performed during but not limited to the wash-in, equilibrium and/or washout phases of neon being present in-vivo. Manipulation of the data produced by an MRI computer and software can include but is not limited to the subtraction of baseline MRI images taken without neon in-vivo in the patient from those taken with neon present in-vivo in the patient, and/or the use of regions of interest to analyze specific areas of any and all images either separately and combined through the use of the MRI computer and software to generate images and/or quantitative data that is of diagnostic and physiological value.

The application of this contrast enhancement agent when used with an MRI system, suitable methodologies and software may include but is not limited to qualitative and quantitative determinations of brain function, and/or local, regional and global cerebral blood flow, and/or steady state cerebrovascular measurements of neurobehavorial stimulation, and/or evaluation of the microvasculature of the brain for changes including but not limited to cerebral blood volume and cerebral blood flow transit times, and/or brain tissue perfusion, and/or blood pool status in other areas of the body, and/or blood flow transit times in other areas of the body, and/or a preferential biologic distribution pattern in other areas of the body and/or tissue blood volume in other areas of the body and/or tissue perfusion in other areas of the body, in the diagnostic evaluation of the status of a patient upon presentation to determine abnormalities and disease states for use in the determination of the probable most effective therapy for a patient including but not limited to physiological challenges and the evaluation of the effectiveness of the therapy(ies) implemented.

While not wishing to be held to any theory, it is postulated that stable neon, whose atomic structure is spherical in terms of its distribution of plus and minus charges, is not polarizable or easily polarizable. Accordingly, a stable neon molecule would not align in any specific direction when subjected to an externally applied magnetic field as would be caused in the practice and use of MRI. Where present in-vivo, it therefore may either dilute or interfere with or otherwise alter the resonating signal of these nuclei and molecules that are polarizable in a magnetic field.

The stable neon may be provided to the living organic subject as pure stable neon or as a mixture of stable neon and one or more other gases such as oxygen, helium, nitrogen or carbon dioxide which are medically pure, commonly referred to as USP or NF. For example, the stable neon may be provided to the patient by inhalation of one hundred percent concentration of pure stable neon gas alternated with a one hundred percent concentration of pure (medical) oxygen gas, or by inhalation of a mixture of stable neon gas and another gas or gases.

The stable neon may be provided to the living organic subject as a gas mixture which may be premixed in a container such as a gas cylinder or may be made up at the use site from containers of the individual gases. If provided as a gas mixture, the mixture, which may be in liquified form and then vaporized for use, comprises from 10 to 80.5 mole percent neon, preferably from 40 to 80.5 mole percent neon, and from 19.5 to 90 mole percent oxygen (medical or USP grade), preferably from 19.5 to 60 mole percent oxygen. The neon mixture may also contain helium which, if present, can be at a concentration of up to 30 mole percent, preferably at a concentration within the range of from 1 to 20 percent. The helium may be useful in more rapidly getting the gas mixture into a patient's bloodstream by reducing the density of the gas mixture increasing the distribution of the stable neon in the air passages of the lungs. The neon mixture may also contain carbon dioxide which, if present, can be at a concentration of up to 7 mole percent, preferably at a concentration within the range of from 0.2 to 5 mole percent. The carbon dioxide may be useful to induce breathing in a patient and thus facilitate the passage of the neon into the patient or as part of a carbon dioxide responsiveness test. The neon mixture may also contain nitrogen, such as when the mixture is made up by mixing neon and air. If present, the nitrogen can be at a concentration of up to 70.5 percent and preferably at a concentration within the range of from 1 to 40 percent. If air is used to make up the neon mixture, the mixture may have present other species in small amounts which may be found in air.

Figure 3A:
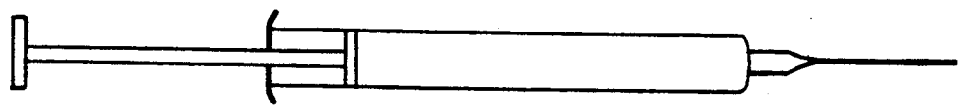
FIG. 3A is a simplified and generic schematic diagram of a medical syringe with needle which may be used for bolus injections for use in the practice of the invention.
Figure 3B:
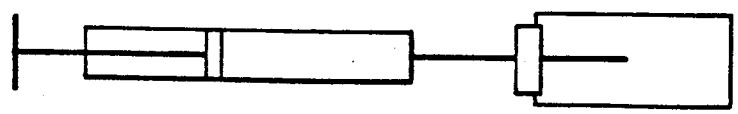
FIG. 3B is a simplified representation of a syringe into which stable neon or a mixture of this invention comprising stable neon is provided from a sealed vial or cartridge.

The neon may be provided to the subject in any effective manner. For example, the stable neon may be provided to the patient by sterile injection of a bolus or infusion using a syringe or other suitable method of injection, wherein the stable neon is injected using sterile technique as a gas or in a equilibrated, saturated or supersaturated solution of sterile water, sterile saline, whole blood or biologic components of blood by syringe, as illustrated in FIG. 3A, or other means of intravenous and/or intraarterial injection. The stable neon or mixture containing stable neon may be provided to the syringe from a sealed vial or other container as illustrated in FIG. 3B. The stable neon gas and/or stable neon gas in solution may be provided to the organic subject in ready to use pre-packaged form in a sterile syringe or cartridge for use with an injection device if the product form allows pre-packaging, provides extended shelf life and can be easily shipped with adequate controls. The syringe or other suitable method of injection or infusion may also be prepared from stable neon gas contained in a sterile vial, disposable or returnable compressed gas cylinder, or stable neon gas from one of those sources or one or more components including but not limited to sterile water, sterile saline, whole blood or biologic components of blood, so long as the final product injected is sterile and aseptic technique is used.

One advantage of the invention is that the contrast enhancement agent need not be administered invasively by intravenous injection or infusion, does not require the withdrawal of human blood and in vitro preparation of the patient's red blood cells with a metallic ion or other element or compound, and does not involve the use of externally sourced biologics as, for example from a vial, such as albumin which can introduce an element of risk into the procedure.

Figure 4:
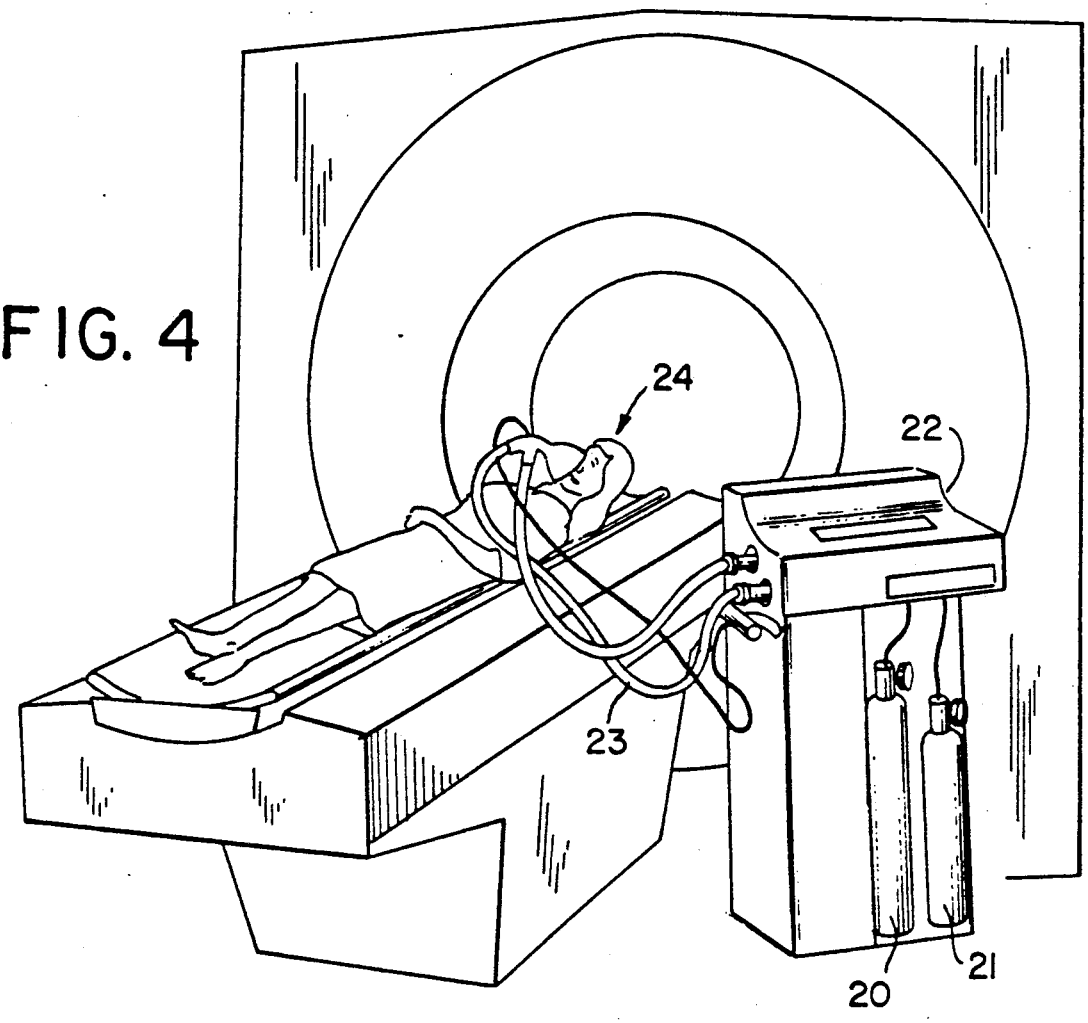
FIG. 4 is a representation of a human subject being given a gas mixture in the practice of the invention.

The stable neon may be delivered to the person or animal non-invasively by alternating inhalation of one hundred percent concentration of stable neon with inhalation of one hundred percent concentration of oxygen during the respiratory cycle, or as part of a gas mixture directly from a cylinder that is pre-mixed with a specific gas mixture containing fixed concentrations of each component or, as illustrated in FIG. 4, from several compressed gas cylinders 20, 21 containing one or more of the gas components which are mixed by a mechanical device 22 and then administered 23 to the patient 24.

The use of helium, if included in the gas mixture, serves to increase the distribution of stable neon in the air passages of the lungs, increasing the access of stable neon to a larger surface area of the alveolar capillary membrane, by reducing the density of the total gas mixture.

The use of carbon dioxide, if included in the gas mixture, serves to alter respiration and/or cerebral physiology at the discretion of the clinician.

An advantage of the invention is its intrinsic safety compared to alternative contrast enhancement agents for use with MRI, and it also possesses many other unique features which make it of benefit as an MRI imaging agent.

Stable neon is non-radioactive, non-toxic, inert, is non-anesthetic at high concentrations and pressures so therefore is non-anesthetic at standard temperatures and pressures of use as an MRI contrast enhancement agent, does not produce any known side effects when breathed by humans and animals for periods of time measured in hours and days at high pressure (which would magnify any side effects) and therefore will produce no known side effects when breathed for the administration times measured in minutes required for an MRI study, has a blood-brain partition coefficient greater than one, has a limited solubility in blood making it rapidly excreted or washed out via the lungs whether administered intravenously by injection or by inhalation, has a low but existing solubility factor in lipids, and will clear rapidly from lipids because of the degree of its solubility in same.

Because of the low but existing solubility in lipids and small molecular size of stable neon, an advantage of the invention may be that it is not limited to intravascular (arterio/venous) spaces but can cross the normal undamaged blood-brain barrier and provide qualitative and quantitative information on cerebral blood flow and brain tissue function. Because of the low solubility of stable neon in lipids and resulting rapid clearance from lipids, and its use with MRI which does not subject the patient to X-rays from an external source as in two or three dimensional X-ray (CT) or a radiation dose from an internal source of injected or inhaled radiopharmaceuticals as in nuclear medicine, an advantage of the invention may be the ability to rapidly repeat studies with no to minimal risk to the patient. This provides the diagnostic advantage of repeat studies being performed at short intervals to challenge physiology using drugs which alter physiology to rapidly assess patient status, determine the proper course of pharmaceutical or surgical therapy to pursue and evaluate the impact of therapy. The lack of X-ray radiation from the invention or the MRI technology it is used with, and the lack of internal radiation as occurs in nuclear medicine from the injection of a radiopharmaceutical, provides the advantage of safely performing procedures with minimal risk to the patient, especially to pediatric patients who are at greatest risk from external and internal radiation dosage.

Another advantage of the invention is that it allows obtaining additional information of value to patient management on the same piece of imaging equipment, thereby reducing the trauma to a patient that may already be in critical condition that may be incurred by transfer of the patient to nuclear medicine or other imaging equipment. Because the patient stays on the same piece of imaging equipment (MRI system) without moving from MRI procedures conducted without and with stable neon being administered, direct anatomical correlation is possible between the images and data produced with and without stable neon. This is an advantage compared to the use of an MRI procedure combined with a nuclear medicine or two or three dimensional X-Ray procedure which are other modalities. The clinician may determine regions of interest to analyze in more detail using and directly comparing the images and data produced with and without stable neon being present in-vivo.

EXAMPLE

This example is presented for illustrative purposes and is not intended to be limiting.

Two whole blood samples were taken from the same human patient and placed in test tubes which were then sealed. Stable neon was provided to one sample and this sample of whole human blood in equilibrium with stable neon in the sealed test tube underwent MRI imaging using an apparatus similar to that illustrated in FIG. 1 using the $T_2$ methodology. The resulting MRI image had a $T_2$ value of 20 milliseconds.

For comparative purposes the procedure was repeated with the other sample except that no stable neon was provided to the sample. The sample had a $T_2$ value of 112 milliseconds. Thus the difference between the sample with and without the neon present was on the order of about 5 to 1.

Furthermore it was found in an additional procedure and using two other samples of whole human blood from the same patient and with the same volume as described above, that when a greater volume of stable neon was provided to the sample of whole human blood, it produced a greater difference in $T_2$ value from that of a whole human blood sample with no stable neon.

Although the invention has been described in detail with reference to certain embodiments, those skilled in the art will recognize that there are other embodiments within the spirit and scope of the claims.

I claim:

1. A method for carrying out magnetic resonance imaging with imProved contrast comprising:
   (A) providing a living organic subject, having nuclei;
   (B) providing stable neon to said subject;
   (C) applying a magnetic field to the subject to align at least some of the subject's nuclei;
   (D) providing radio energy for absorption and re-emission by said aligned nuclei; and
   (E) gathering data based on the re-emitted radio energy to produce an image with improved contrast.

2. The method of claim 1 wherein the stable neon is provided to the subject invasively by injection or infusion.

3. The method of claim 2 wherein the neon is provided in gaseous form.

4. The method of claim 2 wherein the neon is provided as part of an equilibrated, saturated or supersaturated solution.

5. The method of claim 1 wherein the subject is a person or animal and the stable neon is provided to the subject non-invasively by the breathing in of pure neon alternated with the breathing in of pure oxygen.

6. The method of claim 1 wherein the subject is a person or animal and the stable neon is provided non-invasively to the subject by the breathing in of a mixture comprising from 10 to 80.5 mole percent stable neon and from 19.5 to 90 mole percent oxygen.

7. The method of claim 6 wherein the mixture additionally comprises helium in a concentration of up to 30 mole percent.

8. The method of claim 6 wherein the mixture additionally comprises carbon dioxide in a concentration of up to 7 mole percent.

9. The method of claim 6 wherein the mixture additionally comprises nitrogen in a concentration of up to 70.5 mole percent.

10. The method of claim 1 wherein the stable neon is provided to the subject from a cylinder.

11. The method of claim 10 wherein the stable neon is part of a gas mixture within the cylinder.

12. The method of claim 1 wherein the stable neon is provided to the subject as a gas mixture which is prepared at the use site.

13. The method of claim 1 wherein the data gathering of step (E) further comprises establishing qualitative physiological information.

* * * * *